United States Patent
Murai et al.

(10) Patent No.: US 10,787,571 B2
(45) Date of Patent: Sep. 29, 2020

(54) OXIDATION COLOR DEVELOPABLE COMPOUND AND OXIDATION COLOR DEVELOPMENT REAGENT

(71) Applicant: DOJINDO LABORATORIES, Kamimashiki-gun, Kumamoto (JP)

(72) Inventors: Masaki Murai, Kumamoto (JP); Chiaki Matsumoto, Kumamoto (JP); Ryo Sakamoto, Kumamoto (JP); Nobuyuki Ozeki, Kumamoto (JP); Munetaka Ishiyama, Kumamoto (JP)

(73) Assignee: DOJINDO LABORATORIES, Kamimashiki-Gun, Kumamoto (JP)

( * ) Notice: Subject to any disclaimer, the term of this patent is extended or adjusted under 35 U.S.C. 154(b) by 0 days.

(21) Appl. No.: 16/348,235

(22) PCT Filed: Feb. 27, 2018

(86) PCT No.: PCT/JP2018/007339
§ 371 (c)(1),
(2) Date: May 8, 2019

(87) PCT Pub. No.: WO2018/159636
PCT Pub. Date: Sep. 7, 2018

(65) Prior Publication Data
US 2019/0270888 A1   Sep. 5, 2019

(30) Foreign Application Priority Data
Feb. 28, 2017   (JP) ................. 2017-037557

(51) Int. Cl.
*C09B 21/00* (2006.01)
*C12Q 1/28* (2006.01)
*C09B 67/44* (2006.01)

(52) U.S. Cl.
CPC .......... *C09B 21/00* (2013.01); *C09B 67/0083* (2013.01); *C12Q 1/28* (2013.01)

(58) Field of Classification Search
CPC .... C07D 279/22; C09B 21/00; C09B 67/0083
USPC ........................................ 544/37
See application file for complete search history.

(56) References Cited

U.S. PATENT DOCUMENTS

| 4,384,042 A | 5/1983 | Miike et al. |
| 4,879,383 A | 11/1989 | Sakata et al. |

FOREIGN PATENT DOCUMENTS

| JP | S57-029297 A | | 2/1982 | |
| JP | 06032940 A | * | 2/1994 | |
| JP | H06-032940 A | | 2/1994 | |
| JP | H07-121901 B2 | | 12/1995 | |
| JP | 2015-048345 A | | 3/2015 | |
| WO | 2008/047655 A1 | | 4/2008 | |
| WO | WO-2008047655 A1 | * | 4/2008 | ........... C07D 279/30 |

OTHER PUBLICATIONS

Masaki Murai (Dojindo Laboratories) et al., "Development of an Oxidative Colorization Agent with Improved Solubility and Stability in Solution and Application Thereof to a Measurement of Uric Acid," Journal of Analytical Bio-Science, Abstracts of 27th Annual Meeting of the Society of Analytical Bio-Science (at Niigata), 2017, vol. 40, No. 1, The Society of Analytical Bio-Science, p. 57, Published Jan. 13, 2017.

Masaki Murai (Dojindo Laboratories) et al., "Development of an Oxidative Colorization Agent with Improved Solubility and Stability in Solution and Application Thereof to a Measurement of Uric Acid," presented at 27th Annual Meeting of the Society of Analytical Bio-Science in Toki Messe Niigata Convention Center, Niigata, Feb. 11, 2017.

Masaki Murai (Dojindo Laboratories), "Basic Research and Development—Development of an Oxidative Colorization Agent with Improved Solubility and Stability in Solution and Application Thereof to a Measurement of Uric Acid," Program of 27th Annual Meeting of the Society of Analytical Bio-Science (excerpt), p. 17, Saturday, Feb. 11, 2017, 9:48 to 10:48/Venue C.

* cited by examiner

*Primary Examiner* — Kahsay Habte

(57) ABSTRACT

The present invention pertains to: an oxidation color developable compound that is represented by general formula (1), that has excellent solubility in water, and that is less affected by a substance coexisting in a sample; and an oxidation color development reagent using the oxidation color developable compound. In general formula (I), $R^1$, $R^2$, $R^3$, and $R^4$ each represent a straight-chain or branched alkyl group having 1-6 carbon atoms, X represents a hydrophilic functional group, and L represents —$(CH_2)_j$— (j represents an integer of 2-10), —$(CH_2CH_2O)_k$— (k represents an integer of 1-10), or —$(CH_2)_m$—Z—$(CH_2)_n$— (m and n each independently represent an integer of 1-10, and Z represents —$N^+(CH_3)_2$—, —CONH—, —NHCO—, —COO—, —OCO—, —NHCOO—, —OCONH—, —NHCONH—, and —$(CH_2NHCO)_q$—).

1 Claim, 9 Drawing Sheets

OXIDATION COLOR DEVELOPABLE COMPOUND AND OXIDATION COLOR DEVELOPMENT REAGENT

CROSS REFERENCE TO RELATED APPLICATIONS

This patent application is a U.S. national stage application under 35 U.S.C. § 371 of International Patent Application No. PCT/JP2018/007339 filed on Feb. 27, 2018, which claims the benefit of foreign priority to Japanese Patent Application No. JP 2017-037557 filed on Feb. 28, 2017. The International Application was published in Japanese on Sep. 7, 2018, as International. Publication No. WO 2018/159636 A 1 under PCT Article 21(2).

STATEMENT REGARDING PRIOR DISCLOSURES BY THE INVENTOR OR A JOINT INVENTOR

This patent application contains subject matter that was previously disclosed by some of the joint inventors (Masaki MURAL Ryo SAKAMOTO, Nobuyuki OZEKI, and Munetaka ISHIYAMA) in an academic publication, *Journal of Analytical Bio-Science*, 2017 Vol. 40, No. 1, that was published on Jan. 13, 2017, and which included Abstracts of the 27th Annual Meeting of the Society of Analytical Bio-Science, and also previously disclosed by one of the joint inventors (Masaki MURAI) at the 27th Annual Meeting of the Society of Analytical Bio-Science on Feb. 11, 2017.

TECHNICAL FIELD

The invention relates to improvement of oxidative chromogenic compounds and oxidative chromogenic reagents.

BACKGROUND ART

In the field of clinical test, quantification of hydrogen peroxide has been carried out by using a reagent consisting of an oxidative chromogenic compound. For example, the oxidative chromogenic compound having phenothiazine structure as described in Patent Literature 1 (DA-67, FUJIFILM Wako Pure Chemicals corporation. see structural formula shown below) enables high sensitivity measurement because of its high molecular extinction coefficient.

[Chemical Formula 1]

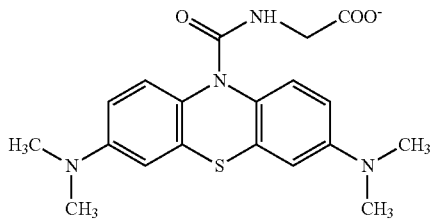

However, DA-67 has a drawback of low optical stability. In view of such problem, for example, a compound having adamantane skeleton of which structural formula is shown below has been proposed as an oxidative chromogenic compound having phenothiazine structure with improved optical stability (see Patent Literature 2).

[Chemical Formula 2]

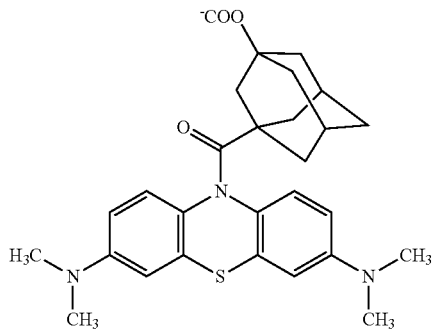

PRIOR ART LITERATURE

Patent Literature

Patent Literature 1: Examined Japanese Patent Application Publication No. H 7-121901.
Patent Literature 2: Unexamined Japanese Patent Application Kokai Publication No. 2015-48345.

DISCLOSURE OF INVENTION

Problem to be Solved by the Invention

However, the compound having phenothiazine structure described in Patent Literature 2 has a problem that the use of the compound as a dry reagent for adding solid oxidative chromogenic compound directly to a sample is difficult because of its low solubility. Moreover, the compound has another problem that it is readily affected by substances coexisting in the sample other than a substrate.

The object of the present invention achieved considering the aforementioned circumstances is to provide an oxidative chromogenic compound having excellent solubility in water and hardly affected by co-existing substances in the sample and an oxidative chromogenic reagent using the same.

Means for Solving the Problem

First aspect of the invention along with the aforementioned object solves the problem as mentioned above by providing an oxidative chromogenic compound represented by General Formula (I) shown below.

[Chemical Formula 3]

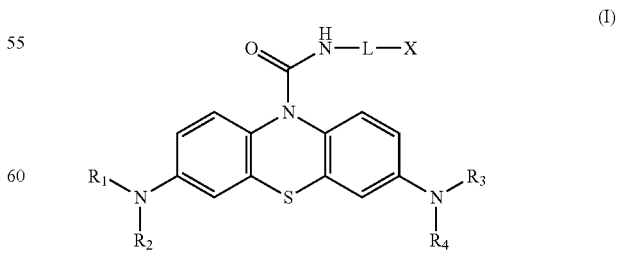

In the General Formula (I) shown above,
$R^1$, $R^2$, $R^3$, and $R^4$ independently represent, a linear or branched alkyl group having 1 to 6 carbon atoms:

X represents a hydrophilic functional group;

L represents an atomic group represented by one of General Formulae (II) to (IV) shown below;

—(CH$_2$)$_j$— (II)

—(CH$_2$CH$_2$O)$_k$— (III)

—(CH$_2$)$_m$—Z—(CH$_2$)$_n$— (IV)

in the General Formula (II) shown above, j represents an integer of 2 to 10;

in the General Formula (III) shown above, k represents an integer of 1 to 10;

in the General Formula (IV) shown above, m and n each independently represents an integer of 1 to 10, Z represents an atomic group selected from a group consisting of —N$^+$(CH$_3$)$_2$—, —CONH—, —NHCO—, —COO—, —OCO—, —NHCOO—, —OCONH—, —NHCONH— and (CH$_2$NHCO)$_q$— (q represents an integer of 1 to 3).

In the oxidative chromogenic compound according to the first aspect of the invention, the hydrophilic functional groups X may be —COO$^-$, —SO$_3^-$, β-cyclodextrin or γ-cyclodextrin.

The oxidative chromogenic compound according to the first aspect of the invention may be represented by any one of Formulae (A) to (H) shown below.

[Chemical Formula 4]

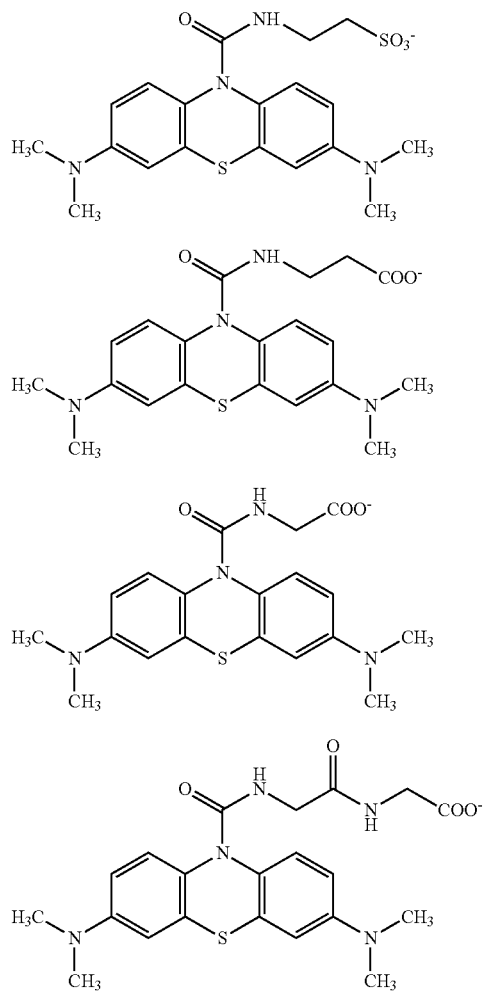

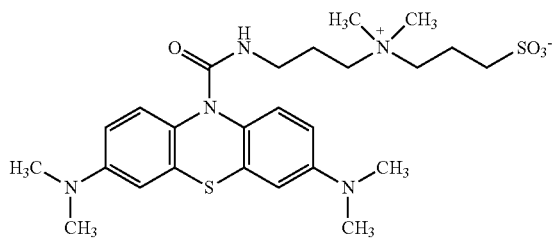

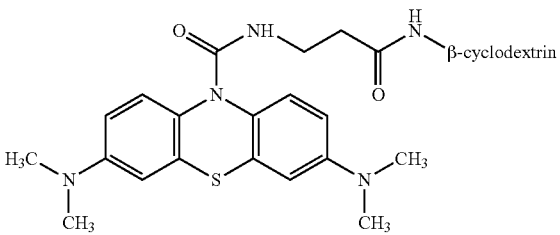

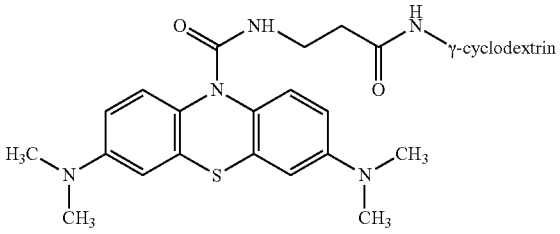

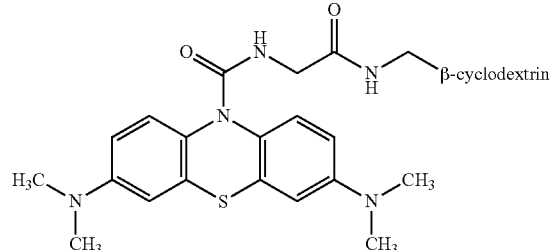

Second aspect of the invention solves the problem as mentioned above by providing an oxidative chromogenic reagent comprising the oxidative chromogenic compound according to the first aspect of the invention.

The oxidative chromogenic reagent according to the second aspect of the invention may be to be used for measuring an oxidation reaction to which a peroxidase involves.

Effect of the Invention

The invention provides an oxidative chromogenic compound superior in both of sensitivity and reliability because it has excellent optical stability and high solubility and it is hardly affected by co-existing substances in the sample and an oxidative chromogenic reagent.

Figure 1:
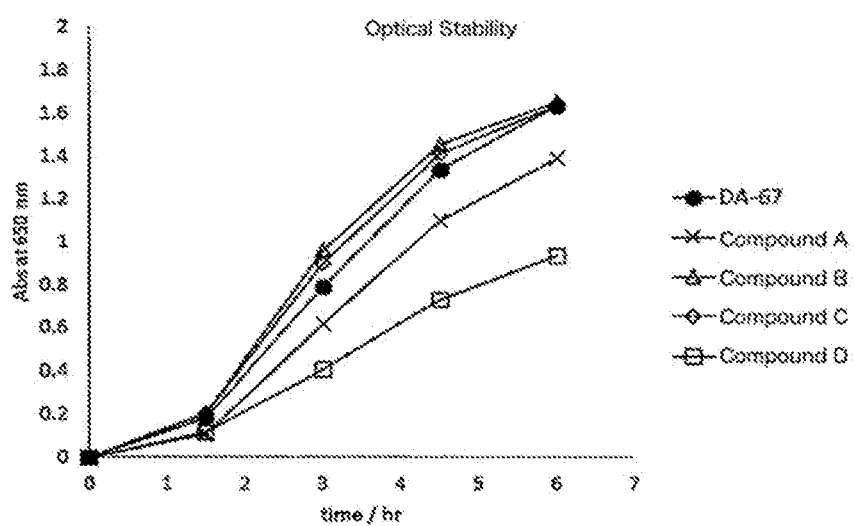
FIG. 1 shows the optical stability of the compound according to the invention used as the oxidative chromogenic reagent in comparison with a conventional reagent.

The oxidative chromogenic compound according to first embodiment of the invention (hereinafter it may be abbreviated to "oxidative chromogenic compound") is represented by the General Formula (I) shown below.

[Chemical Formula 5]

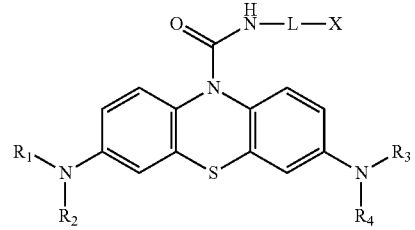

(I)

In the General Formula (I) shown above,
$R^1$, $R^2$, $R^3$, and $R^4$ independently represent, a linear or branched alkyl group having 1 to 6 carbon atoms:
X represents a hydrophilic functional group;
L represents an atomic group represented by one of General Formulae (II) to (IV) shown below;

$$—(CH_2)_j— \quad (II)$$

$$—(CH_2CH_2O)_k— \quad (III)$$

$$—(CH_2)_m—Z—(CH_2)_n— \quad (IV)$$

in the General Formula (II) shown above, j represents an integer of 2 to 10;
in the General Formula (III) shown above, k represents an integer of 1 to 10;
in the General Formula (IV) shown above, m and n each independently represents an integer of 1 to 10, Z represents an atomic group selected from a group consisting of —N$^+$(CH$_3$)$_2$—, —CONH—, —NHCO—, —COO—, —OCO—, —NHCOO—, —OCONH—, —NHCONH— and —(CH$_2$NHCO)$_q$— (q represents an integer of 1 to 3).

As a linker L for linking phenothiazine structure and hydrophilic functional group X, any atomic group may be employed as long as it does not affect water solubility, optical stability, influence of coexisting substances in the sample etc. of the oxidative chromogenic compound. Example of the L includes —(CH$_2$)$_2$—, —(CH$_2$)$_3$—, —(CH$_2$CH$_2$O)—, —(CH$_2$CH$_2$O)$_2$—, —(CH$_2$)—CONH—(CH$_2$)—, —(CH$_2$)$_2$—CONH—(CH$_2$)$_2$— and —(CH$_2$)$_3$—N$^+$(CH$_3$)$_2$—(CH$_2$)$_3$—.

Example of linear or branched alkyl group $R^1$, $R^2$, $R^3$, and $R^4$ includes methyl group, ethyl group, n-propyl group and isopropyl group, preferably methyl group.

Example of hydrophilic functional group X includes —COOH, —SO$_3$H, —COO$^-$, —SO$_3^-$, β-cyclodextrin or γ-cyclodextrin. The groups —COO$^-$ and —SO$_3^-$ may be any salts such as alkali metal salts, alkaline earth metal salts and ammonium salts.

Preferred examples of the oxidative chromogenic compound include the compound represented by the Formulae (A) to (H) shown below.

[Chemical Formula 6]

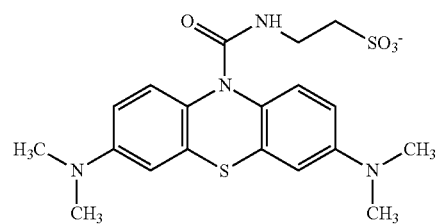

(A)

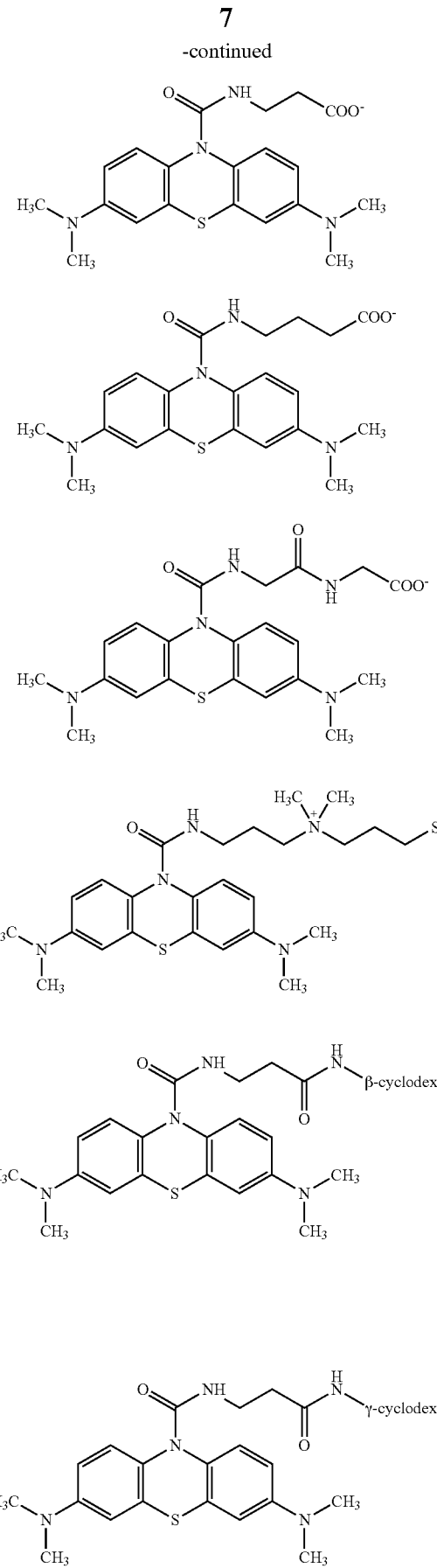

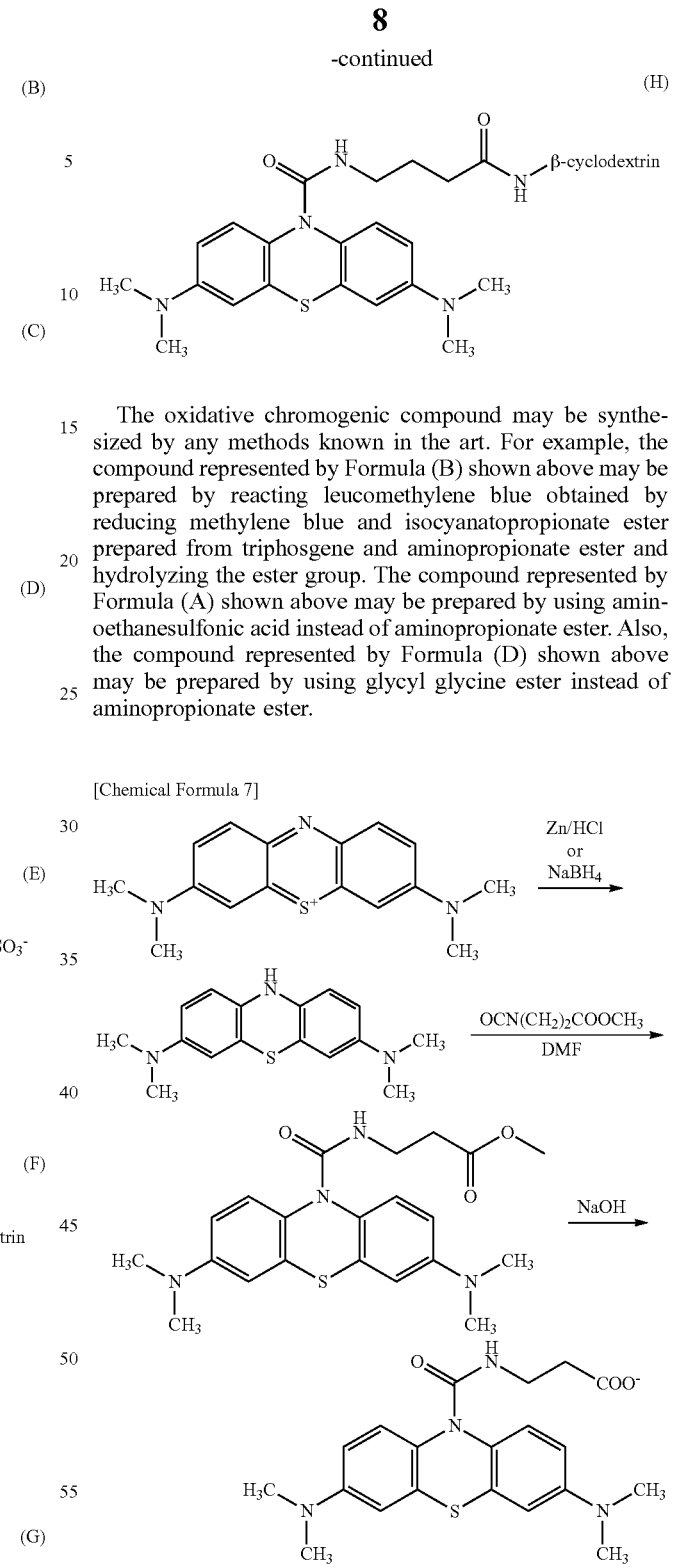

The oxidative chromogenic compound may be synthesized by any methods known in the art. For example, the compound represented by Formula (B) shown above may be prepared by reacting leucomethylene blue obtained by reducing methylene blue and isocyanatopropionate ester prepared from triphosgene and aminopropionate ester and hydrolyzing the ester group. The compound represented by Formula (A) shown above may be prepared by using aminoethanesulfonic acid instead of aminopropionate ester. Also, the compound represented by Formula (D) shown above may be prepared by using glycyl glycine ester instead of aminopropionate ester.

[Chemical Formula 7]

The oxidative chromogenic compound maintains the characteristics of phenothiazine of high molecular distinction coefficient that enables high sensitivity measurement and has high solubility in water. Therefore, it may be used, as a dry reagent for adding the solid reagent directly to the sample without dissolving in water or a water-soluble organic solvent in advance. In addition, the oxidative chromogenic compound has high optical stability and is hardly affected by co-existing substances in biological samples such as conjugated bilirubin and glutathione, which enables high sensitivity and highly reliable quantitative analysis of target substances.

The oxidative chromogenic reagent according to second embodiment of the invention comprises the oxidative chromogenic compound according to the first embodiment of the invention as described above. Particularly preferable application of the oxidative chromogenic reagent includes the measurement of the oxidation reaction in which peroxidase involves. In other words, concentration of hydrogen peroxide, activity of peroxidase and the like may be determined quantitatively from the absorbance of the spectrum of the colored oxidative chromogenic reagent measured by adding the oxidative chromogenic reagent to the target sample.

In addition, the oxidative chromogenic compound is oxidized and colored by an oxidative substance. The other applications using such property of the oxidative chromogenic compound is possible. For example, the oxidative chromogenic compound is oxidized and colored by chlorine, which may be applicable to a measurement of residual chlorine concentration in water. In other words, the residual chlorine concentration may be determined from the absorbance of the absorption spectrum of the sample to which the compound according to the present invention is added and colored.

EXAMPLES

The present invention will be illustrated by referring the examples carried out to confirm the action and the effect of the present invention.

Example 1: Synthesis of Oxidative Chromogenic Compound

The compounds represented by the formulae (A), (B), (C) and (D) shown above (hereinafter, referred to "Compound A (according to the present invention)", "Compound B (according to the present invention)", "Compound C (according to the present invention)" and "Compound D (according to the present invention)", respectively) were synthesized according to scheme (I) to (X) shown below.

[Chemical Formula 8]

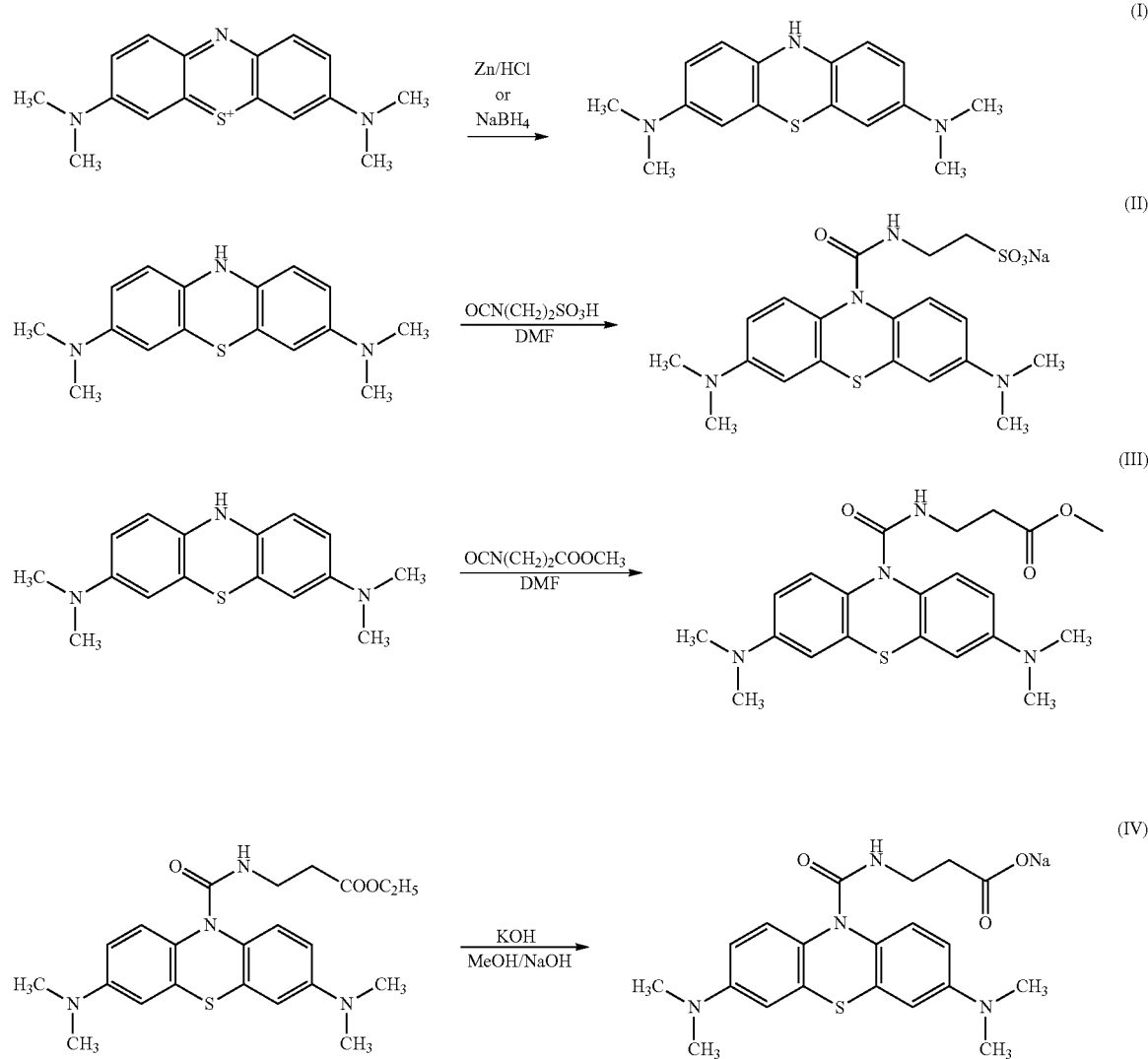

-continued
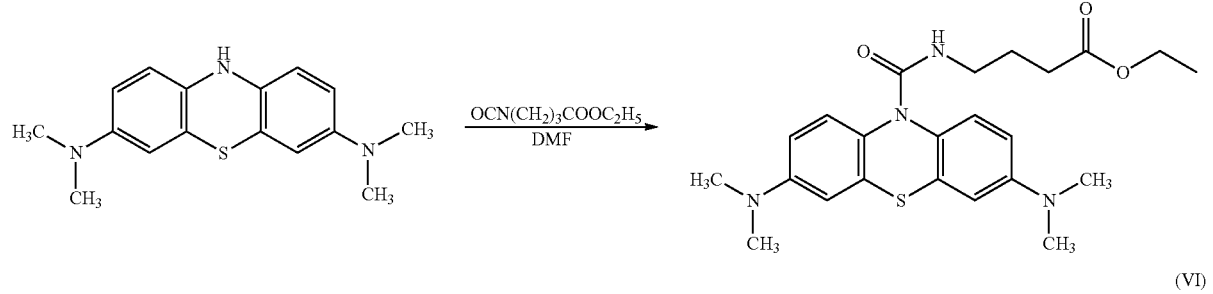
(V)
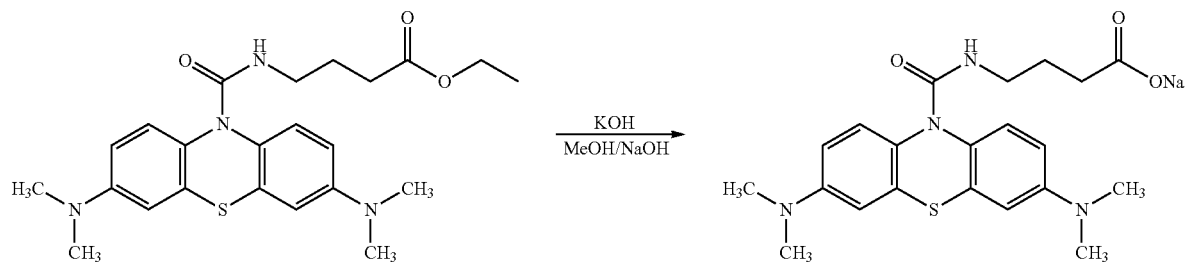
(VI)
[Chemical Formula 9]
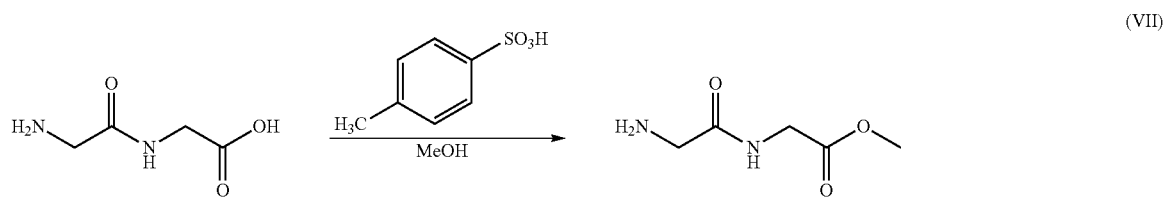
(VII)
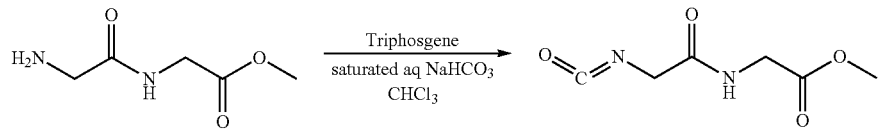
(VIII)
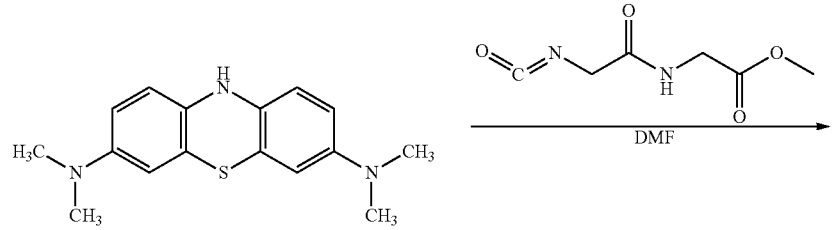
(IX)
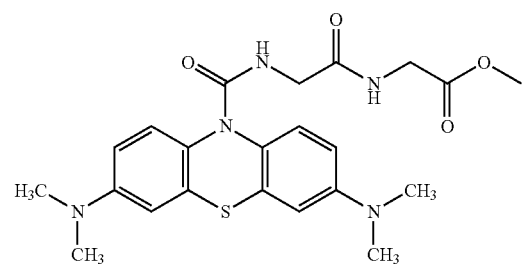

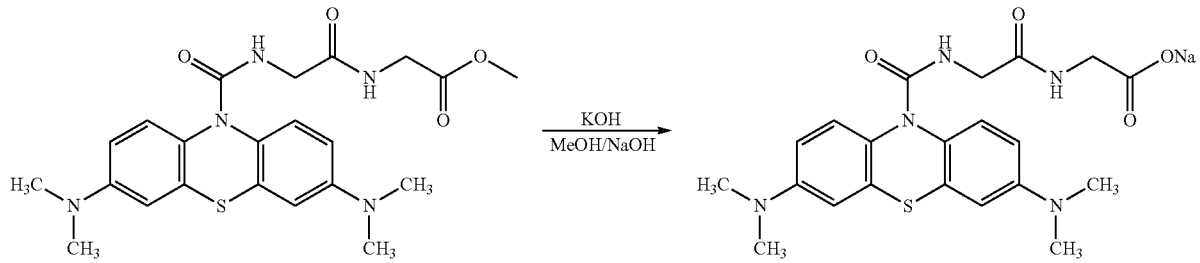

<Synthesis of Compound A>

According to Scheme (1) shown above, leucomethylene blue was prepared as follows. 81.5 g (0.218 mol) of methylene blue was placed in a 3 L round bottomed flask, 1.3 L of pure water added and heated to dissolve while irradiating ultrasonic wave. 1.3 L of chloroform was added with stirring magnetically and aqueous solution of $NaBH_4$ was added dropwise. Chloroform layer was separated, dried over sodium sulfate and filtrated through a pleated filter paper. The chloroform layer was concentrated to dryness, which afforded 65 g of pale blue powder. This intermediate was used in the preparation of Compound A, B, C and D.

Compound A according to the invention was synthesized according to Scheme (II) shown above. 2.32 g (8.12 mmol) of leucomethylene blue synthesized as above was placed in a 500 mL of round bottomed flask, 100 mL of DMF was added and stirred magnetically to dissolve. Isocyanatotaurine was prepared otherwise as follows: 2.03 g (16.24 mmol) of tauline was added to 100 mL of chloroform and 100 ml of saturated aqueous solution of sodium carbonate placed in a 500 mL round bottomed flask, to which 1.6 g (5.41 mmol) of triphosgene was added while stirring on an ice bath and the mixture was stirred for 30 minutes. Isocyanatotaurine was added to the leucomethylene blue and reacted for 17 hours at room temperature. After the reaction, the reaction liquid was concentrated to dryness, pH was adjusted to 12 with sodium hydroxide and the product was purified by a column chromatography. Purification by the column chromatography afforded 640 mg of pale blue powder.

Identification data: $^1$H-NMR (400 MHz, $D_2O$) δ: 2.64 (s, 12H), 2.86-2.89 (dd, 2H, J=12 Hz), 3.37-3.40 (dd, 2H, J=12H), 6.61-6.68 (m, 4H, J=28 Hz), 7.07-7.09 (d, 2H, J=8 Hz).

<Synthesis of Compound B>

According to Scheme (III) shown above, methyl ester derivative, an intermediate of Compound B according to the invention was synthesized as follows. 985 mg (3.45 mmol) of leucomethylene blue synthesized above was placed in a 100 mL of round bottomed flask, 50 mL of DMF was added and stirred magnetically to dissolve. Isocyanato-β-alanine methyl ester prepared otherwise from 1.45 g (10.35 mmol) β-alanine methyl ester hydrochloric salt and 1.02 g (3.45 mmol) of triphosgene was added and the mixture was stirred for 3 hours. After the reaction, the reaction liquid was concentrated to dryness and purified with a column chromatography. Purification of the column chromatography afforded 1.317 g of deep blue powder.

According to Scheme (IV) shown above, Compound B according to the invention was synthesized as follows. 1.317 g (3.3 mmol) of the methyl ester derivative and 100 mL of methanol was placed in a 100 mL round bottomed flask and heated to dissolve. 3.3 mL (3.3 mmol) of 1 mol/L KOH/methanol solution was added and the mixture was concentrated to dryness. After the concentration to dryness, the residue was dissolved in 100 mL of methanol and concentrated to dryness again. The operation was repeated three times. After adjusting the pH to 12 by sodium hydroxide, the product was purified by a column chromatography. Purification by the column chromatography afforded 520 mg of pale blue powder.

Identification data: $^1$H-NMR (400 MHz, DMSO-$d_6$) δ: 1.95-1.97 (dd, 2H, J=8 Hz), 3.05 (s, 12H), 3.09-3.13 (m, 2H, J=16 Hz), 6.62-6.68 (m, 4H. J=24H), 6.84-6.86 (dd, 1H, J=8 Hz), 7.23-7.25 (d, 2H, J=8 Hz).

<Synthesis of Compound C>

According to Scheme (V) shown above, ethyl ester derivative, an intermediate of Compound C according to the invention was synthesized as follows. 2.77 g (9.69 mmol) of leucomethylene blue synthesized above was placed in a 500 mL of round bottomed flask, 300 mL of DMF was added and stirred magnetically to dissolve. Isocyanatobutanoic acid ethyl ester prepared otherwise from 3249 mg (19.38 mmol) ethyl 4-aminobutanoate hydrochloric salt and 1.92 g (6.46 mmol) of triphosgene was added and the mixture was stirred for 3 hours. After the reaction, the reaction liquid was concentrated to dryness and purified with a column chromatography. Purification of the column chromatography afforded 4.36 g of deep blue powder.

According to Scheme (VI) shown above, Compound C according to the invention was synthesized as follows. 4.36 g (9.85 mmol) of the ethyl ester derivative and 100 mL of methanol was placed in a 200 mL round bottomed flask and heated to dissolve. 9.85 mL (9.85 mmol) of 1 mol/L KOH/methanol solution was added and the mixture was concentrated to dryness. After the concentration to dryness, the residue was dissolved in 100 mL of methanol and concentrated to dryness again. The operation was repeated three times. After adjusting the pH to 12 by sodium hydroxide, the product was purified by a column chromatography. Purification by the column chromatography afforded 900 mg of blue powder.

$^1$H-NMR (400 MHz, DMSO-$d_6$) δ: 1.50-1.53 (m, 2H, J=12 Hz), 1.78-1.81 (dd, 2H, J=12H), 2.88 (s, 12H), 2.88 (s, 12H), 3.04-3.07 (dd, 1H, J=12 Hz), 6.11-6.14 (dd, 1H, J=12 Hz), 6.84-6.86 (m, 4H, J=16 Hz), 7.25-7.27 (d, 2H, J=8 Hz).

<Synthesis of Compound D>

According to Scheme (VII) shown above, glycyl glycine methyl ester derivative. an intermediate of Compound C according to the invention was synthesized as follows. 5000 mg (37.84 mmol) of glycyl glycine, 200 mL of methanol and 7167 mg (41.62 mmol) of p-toluenesulfonic acid monohydrate were placed in 500 mL round bottomed flask and irradiated with ultrasonic wave to dissolve. The reaction liquid was concentrated to dryness. After the concentration to dryness, the residue was dissolved in 100 mL of methanol and concentrated to dryness again. The operation was repeated three times. 11.5 g of white crystal was obtained.

According to Scheme (VIII) and (IX) shown above, methyl ester derivative, an intermediate of Compound D according to the invention was synthesized as follows. 3.35 g (11.75 mmol) of leucomethylene blue synthesized above was placed in a 300 mL of round bottomed flask, 200 mL of DMF was added and stirred magnetically to dissolve. Isocyanatoglycyl glycine methyl ester prepared otherwise from 3435 mg (23.5 mmol) methyl ester derivative of glycyl glycine and 2.32 g (7.83 mmol) of triphosgene was added and the mixture was stirred for 18 hours. After the reaction, the reaction liquid was concentrated to dryness and purified with a column chromatography. Purification of the column chromatography afforded 2.97 g of deep blue powder.

According to Scheme (X) shown above, Compound D according to the invention was synthesized as follows. 2.97 g (6.49 mmol) of the methyl ester derivative and 100 mL of methanol was placed in a 200 mL round bottomed flask and heated to dissolve. 6.49 mL (6.49 mmol) of 1 mol/L KOH/methanol solution was added and the mixture was concentrated to dryness. After the concentration to dryness, the residue was dissolved in 100 mL of methanol and concentrated to dryness again. The operation was repeated three times. After adjusting the pH to 12 by sodium hydroxide, the product was purified by a column chromatography. Purification by the column chromatography afforded 440 mg of blue powder.

Identification data: $^1$H-NMR (400 MHz, $D_2O$) δ: 2.64 (s, 12H), 3.63 (s, 2H), 3.69 (s, 2H), 6.62-6.69 (m, 4H, J=28 Hz), 7.14-7.17 (d. 2H, J=8 Hz).

Example 2: Evaluation of Properties of Oxidative Chromogenic Compound

Comparison of Compound A, B, C and D as the oxidative chromogenic compounds according to the invention with a conventional oxidative chromogenic reagent DA-67 were made with respect to following items.

<Solution Stability>

Solution stability under photo irradiation was tested as follows. Each sample solution of Compound A, B, C and D according to the invention and DA-67 was prepared with 50 mM MES buffer (pH 6.5) in the concentration of 0.25 mM. Temporal change in the absorbance at 650 nm of each reagent prepared placed under fluorescent lamp was monitored. The results are shown in FIG. 1. Order of the optical stability was DA-67 ≃Compound B according to the invention≃Compound C according to the invention<Compound A according to the invention<Compound D according to the invention. Stability of all compounds according to the invention were comparable to or higher than that of DA-67.

<Evaluation of Interference (Evaluation of Influence of Contaminants)>

Magnitude of interference were evaluated using hemolytic hemoglobin (Hb), bilirubin-F (BIL-F) and bilirubin-C (BIL-C) as contaminants. Each solution was prepared as follows.

Figure 2:
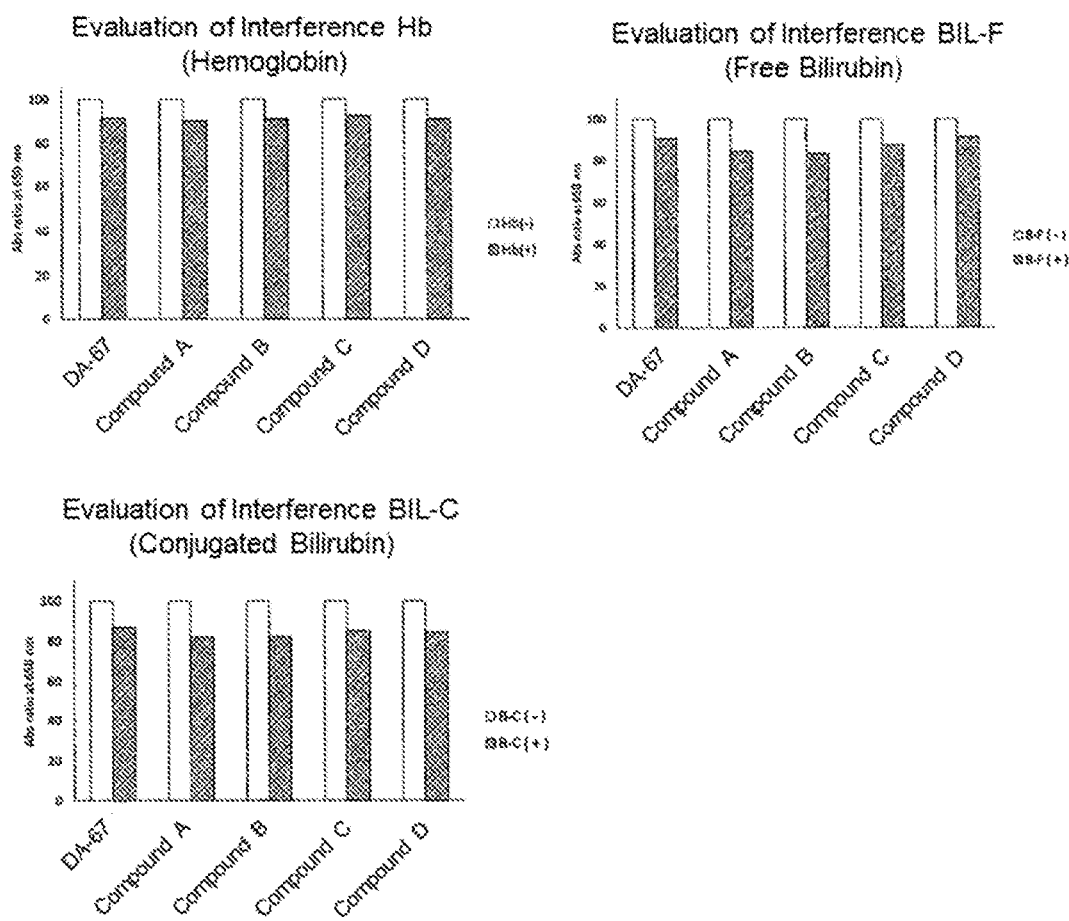
FIG. 2 shows the influence of contaminants to the compound according to the invention used as the oxidative chromogenic reagent in comparison with a conventional reagent.

Oxidative chromogenic reagent (Compound A, B, C and D according to the invention and DA-67)+POD: 3 mM solutions of the oxidative chromogenic reagents were prepared by dissolving the oxidative chromogenic reagent in 50 mM MES buffer (pH 6.5). POD was added to the solutions and made to 4.5 mL by ultra-pure water. Solutions for evaluating interference: the solution in each bottle was dissolved in 2 mL of ultra-pure water and diluted to 10 times. $H_2O_2$/buffer solution: 300 μL of 1 mM aqueous solution of $H_2O_2$ and 5 mL of buffer were mixed. The results are shown in FIG. 2. The influence of the contaminants on the compounds according to the invention is comparable to that on DA-67.

<Influence of pH>

The influence of pH on Compound A, B, C and D according to the invention and DA-67 was evaluated by measuring the absorbance at 650 nm in pH 5.5, 6.5 and 7.5. Each solution was prepared as follows.

Figure 3:
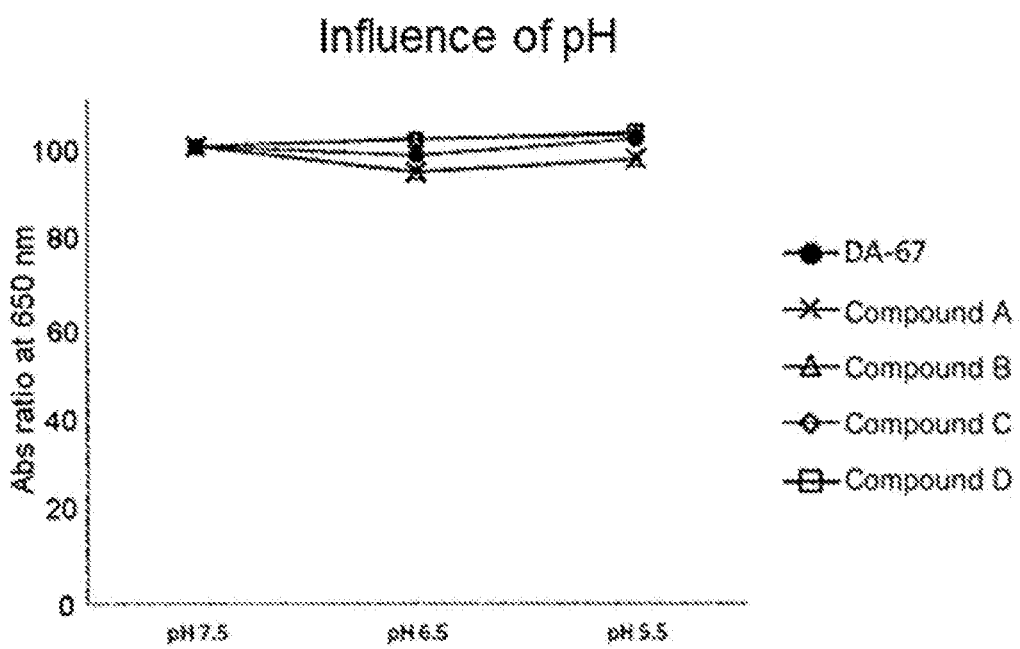
FIG. 3 shows the influence of pH to the compound according to the invention used as the oxidative chromogenic reagent in comparison with a conventional reagent.

Oxidative chromogenic reagent (Compound A, B, C and D according to the invention and DA-67)+POD: 3 mM solutions of the oxidative chromogenic reagents were prepared by dissolving the oxidative chromogenic reagent in 50 mM MES buffer (pH 5.5), 50 mM MES buffer (pH 6.5) and 50 mM HEPES buffer (pH 7.5). POD was added to the solutions and made to 4.5 mL by ultra-pure water. $H_2O_2$/buffer solution: 300 μL of 1 mM aqueous solution of $H_2O_2$ and 5 mL of buffer were mixed. The results are shown in FIG. 3. The influence of the pH on the compounds according to the invention is comparable to that on DA-67.

<Influence of GSH>

The influence of GSH (glutathione in reduced form) on Compound A, B, C and D according to the invention and DA-67 was evaluated. Each solution was prepared as follows.

Figure 4:
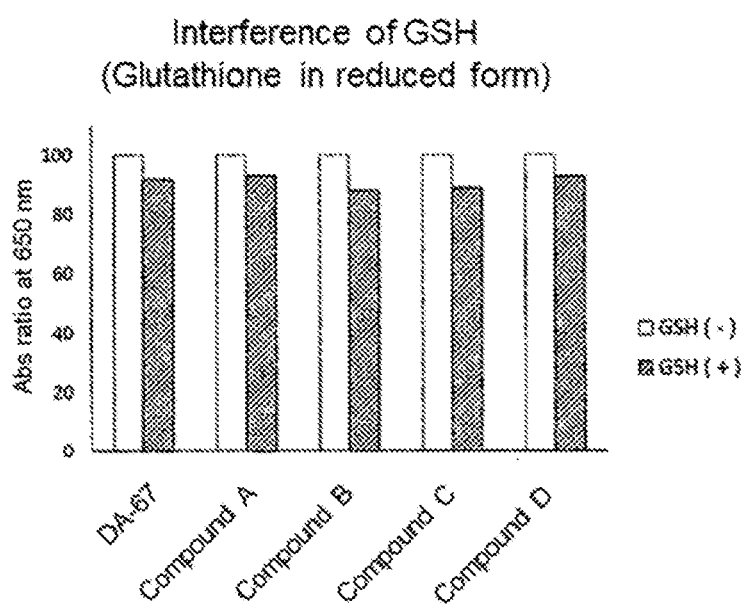
FIG. 4 shows the influence of GSH (glutathione in reduced form) to the compound according to the invention used as the oxidative chromogenic reagent in comparison with a conventional reagent.

Oxidative chromogenic reagent (Compound A, B, C and D according to the invention and DA-67)+POD: 3 mM solutions of the oxidative chromogenic reagents were prepared by dissolving the oxidative chromogenic reagent in 50 mM HEPES buffer (pH 7.5). POD was added to the solutions and made to 4.5 mL by ultra-pure water. $H_2O_2$/buffer solution: 300 μL of 1 mM aqueous solution of $H_2O_2$ and 5 mL of buffer were mixed. GSH/ultra-pure water solution: 10 μL of 10 mM aqueous solution of GSH and 200 μM buffer were mixed. The results are shown in FIG. 4. The influence of GSH (glutathione in reduced form) on the compounds according to the invention is comparable to that on DA-67.

<Influence of BSA>

The influence of BSA (bovine serum albumin) on Compound A, B, C and D according to the invention and DA-67 was evaluated. Each solution was prepared as follows.

Figure 5:
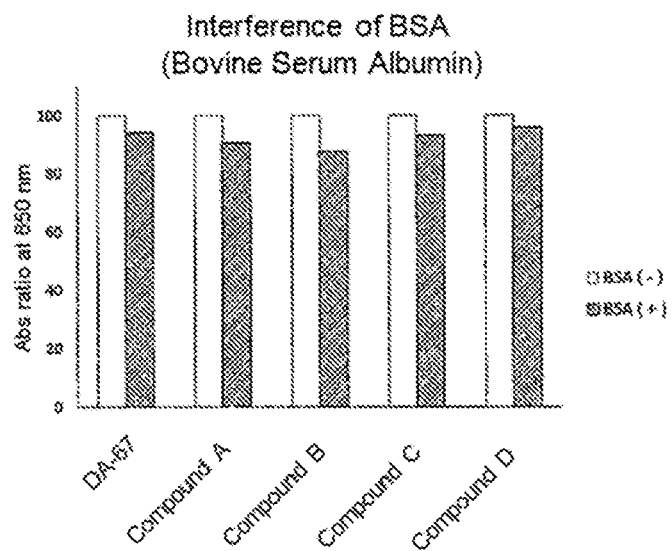
FIG. 5 shows the influence of BSA (bovine serum albumin) to the compound according to the invention used as the oxidative chromogenic reagent in comparison with a conventional reagent.

Oxidative chromogenic reagent (Compound A, B, C and D according to the invention and DA-67)+POD: 3 mM solutions of the oxidative chromogenic reagents were prepared by dissolving the oxidative chromogenic reagent in 50 mM HEPES buffer (pH 7.5). POD was added to the solutions and made to 4.5 mL by ultra-pure water. $H_2O_2$/buffer solution: 300 μL of 1 mM aqueous solution of $H_2O_2$ and 5 mL of buffer were mixed. BSA/ultra-pure water solution: 10 μL of 20% BSA solution and 200 μM buffer were mixed. The results are shown in FIG. 5. The influence of BSA (bovine serum albumin) on the compounds according to the invention is comparable to that on DA-67.

<Solubility in Water>

DA-67 has a drawback of poor solubility in water in addition to the optical stability. The difference in the solubility in water of Compound A, B, C and D according to the invention and DA-67 was evaluated. Each solution was prepared as follows.

3 mM of the solutions of the oxidative chromogenic reagents (Compound A, B, C and D according to the invention and DA-67) were prepared by dissolving the oxidative chromogenic reagent in ultra-pure water by heating operation (+) or without heating operation (−). After filtrating the solutions, difference in the solubility in water was evaluated based on the ratio of peak area of HPLC analysis.

Condition of HPLC Analysis

| | |
|---|---|
| <Column> | Inertsil ODS-3, φ4.6 × 150 mm |
| <Temperature> | 40° C. |
| <Eluent> | 0.1% TFA aqueous solution/acetonitrile = 20/80 |
| <Flow rate> | 1.0 mL/min |
| <Detector> | UV 254 nm |
| <Sample volume> | 5 μL injected |
| <Detection time> | 15 minutes |

Figure 6:
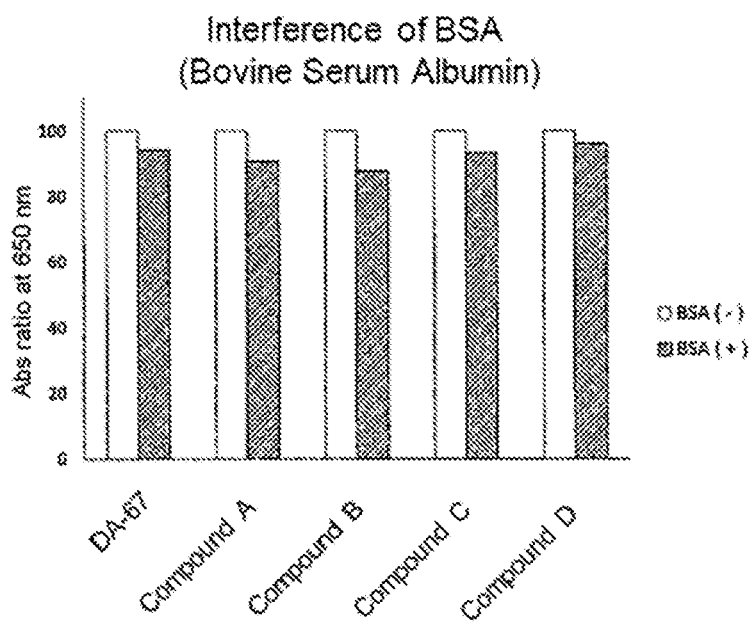
FIG. 6 shows the solubility of the compound according to the invention in water in comparison with a conventional reagent.
Figure 7:
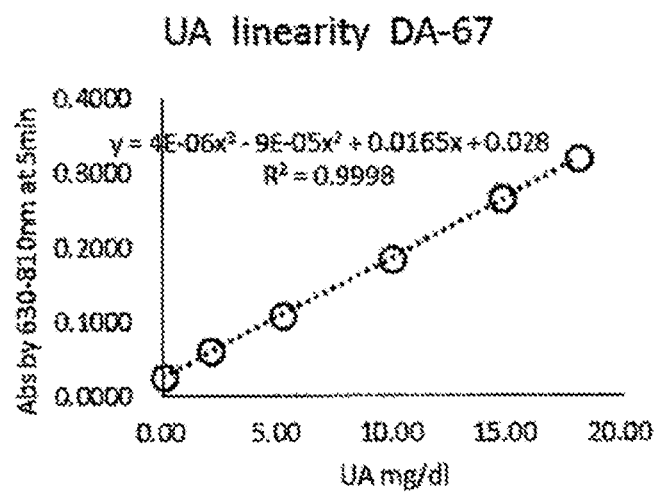
FIG. 7 shows linearity and blank coloring of a conventional compound used as an oxidative chromogenic reagent among evaluation items in the quantification of UA (uric acid).
Figure 8:
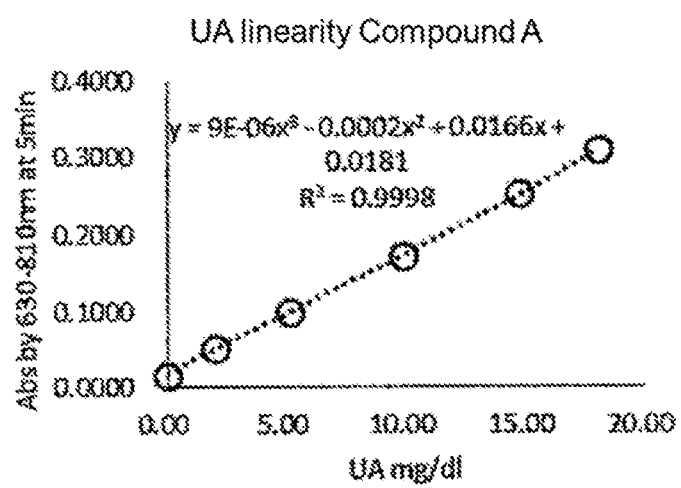
FIG. 8 shows linearity and blank coloring of Compound A according to the invention used as an oxidative chromogenic reagent among evaluation items in the quantification of UA (uric acid).
Figure 9:
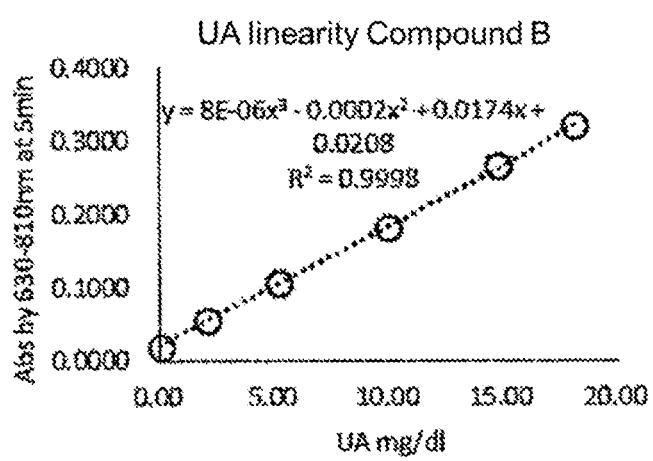
FIG. 9 shows linearity and blank coloring of Compound B according to the invention used as an oxidative chromogenic reagent among evaluation items in the quantification of UA (uric acid).
Figure 10:
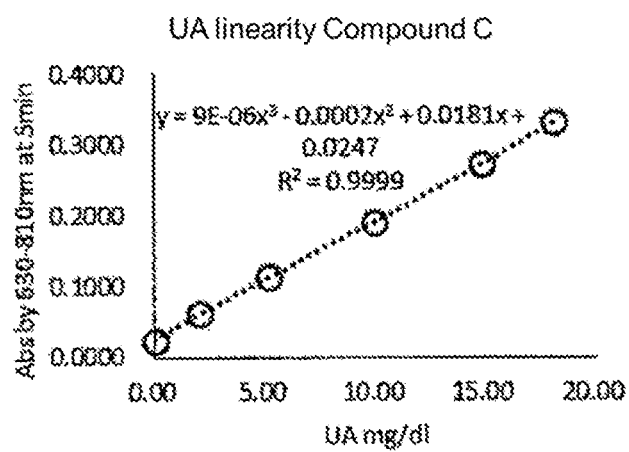
FIG. 10 shows linearity and blank coloring of Compound C according to the invention used as an oxidative chromogenic reagent among evaluation items in the quantification of UA (uric acid).
Figure 11:
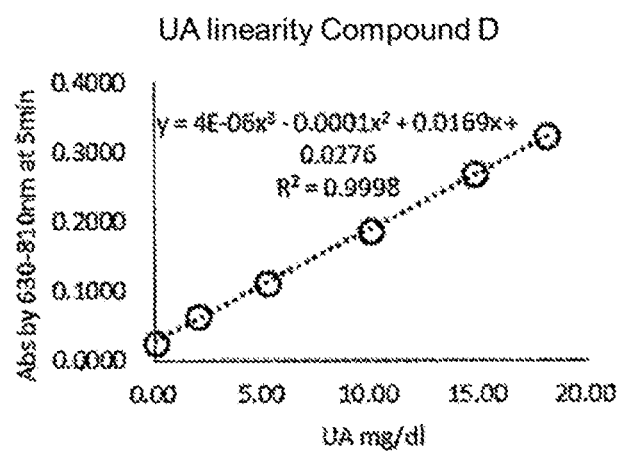
FIG. 11 shows linearity and blank coloring of Compound D according to the invention used as an oxidative chromogenic reagent among evaluation items in the quantification of UA (uric acid).

The results are shown in FIG. 6. The solubility of the compounds according to the invention in water is improved in comparison with DA-67.

<Linearity Among Evaluation Items in the Quantification of UA (Uric Acid)>

Figure 12:
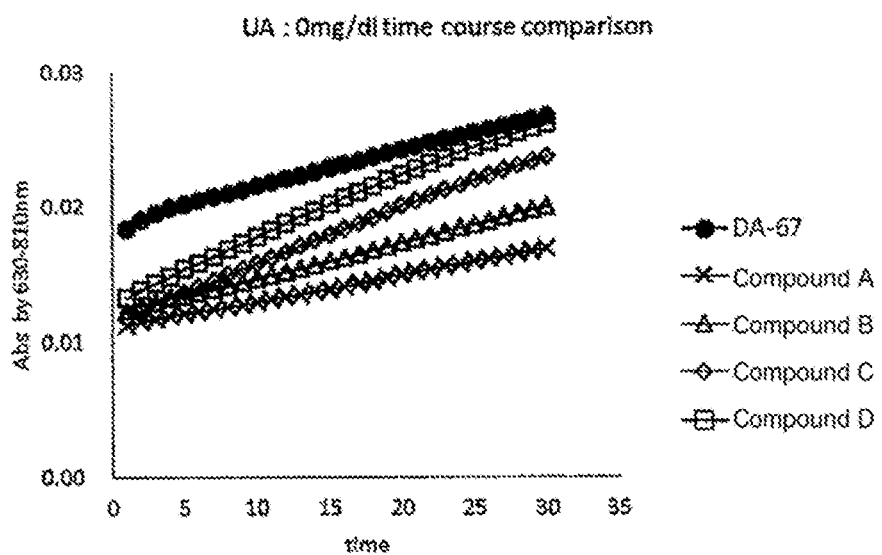
FIG. 12 shows linearity and blank coloring of the compounds according to the invention used as an oxidative chromogenic reagent among evaluation items in the quantification of UA (uric acid) in comparison with a conventional reagent.

Comparison of linearity in the range of UA concentration of 0 to 20 mg/dL was carried out. The data sampled was converted to absorbance by arithmetic processing using a special algorithm. The results are shown in FIGS. 7 to 11. The temporal change of the blank coloring of each compound is shown in FIG. 12. Linearity of Compound A, B, C and D according to the invention is comparable to that on DA-67. Blank coloring of Compound A, B. C and D according to the invention is superior to that of DA-67.

<Evaluation of Interference (Evaluation of Influence of Contaminant) Among Evaluation Items in the Quantification of UA (Uric Acid)>

Figure 13:
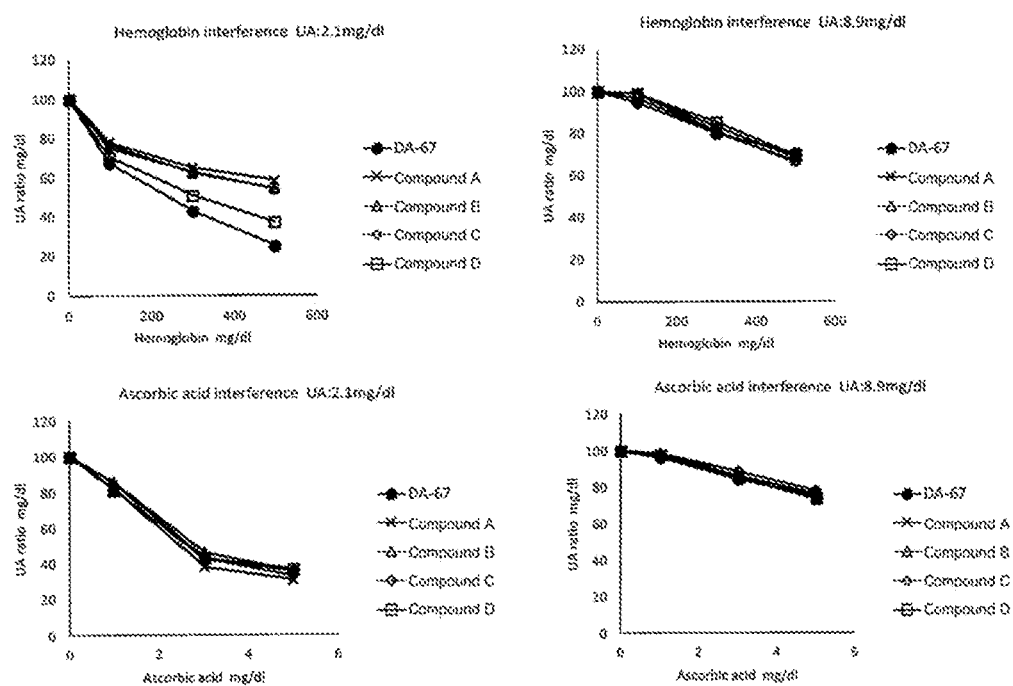
FIG. 13 shows influence of contaminants on the compounds according to the invention used as an oxidative chromogenic reagent among evaluation items in the quantification of UA (uric acid) in comparison with a conventional reagent.

Magnitude of interference were evaluated using hemolytic hemoglobin (Hb), ascorbic acid and bilirubin-C (BIL-C) as contaminants. The data was converted to the concentration using third order regression formula obtained from the linearity test and the variation of average of converted concentration of five measurements of each concentration of the contaminants was calculated and compared. The results are shown in FIG. 13. The interference of ascorbic acid and bilirubin-C (BIL-C) to all of the compounds according to the invention was comparable to that to DA-67 at low and high concentration regions. The interference of hemolytic hemoglobin (Hb) to all of the compounds according to the invention was comparable to that to DA-67 at high concentration region but superior to that to DA-67 at low concentration region.

<Accelerated Stability Among Evaluation Items in the Quantification of UA (Uric Acid)>

Figure 14:
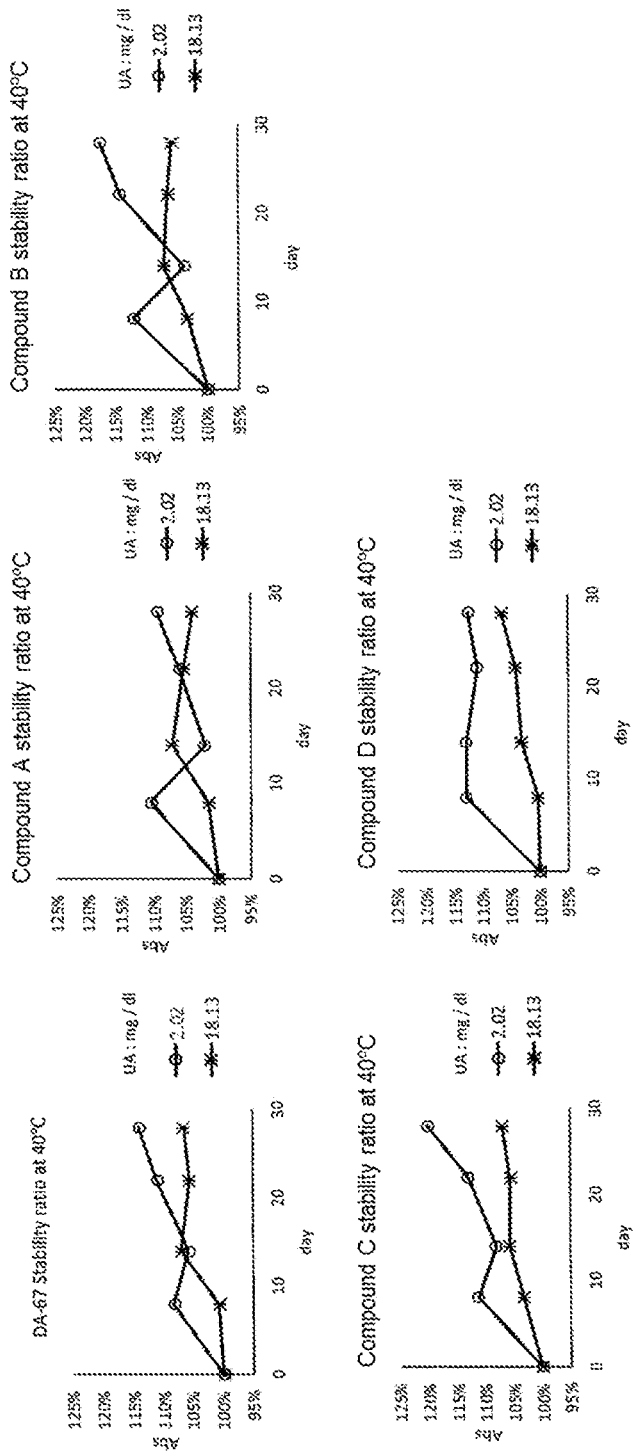
FIG. 14 shows influence of accelerated stability on the compounds according to the invention used as an oxidative chromogenic reagent among evaluation items in the quantification of UA (uric acid) in comparison with a conventional reagent Embodiments of the Invention For better understanding the invention, embodiments of the invention will be illustrated.

At day 7, 14, 21 and 28, the reagents (wrapped with aluminum foil) stored in a chamber at 40° C. were taken out and brought back to room temperature. Also, the samples were taken out of a freezing chamber and naturally thawed at room temperature. They were mixed on a vortex mixer and used for the measurement. The absorbance was measurement similarly to the measurement of the linearity. The results are shown in FIG. 14. The accelerated stabilities of the all compounds according to the invention at high concentration region of UA (18.13 mg/dL) were comparable to that on DA-67. The order of accelerated stabilities of the all compounds according to the invention at low concentration region of UA (2.1 mg/dL) were Compound A according to the invention>Compound D according to the invention≈DA-67>Compound B according to the invention>Compound C according to the invention.

Various embodiments and variations of the invention may be possible without departing from the broad spirit and scope of the invention. The embodiments and examples as mentioned above are provided for illustrating the invention, not for limiting the scope of the invention. In other words, the scope of the invention is defined by attached Claims, not by the embodiments and examples. In addition, various variations made within the scope of the Claims and within the scope of the equivalent of the invention should be within the scope of the invention. The present application claims the priority based on Japanese Patent Application 2017-37557 filed on Feb. 28, 2017 including the specification, claims, drawings and abstract thereof. The entire disclosure in the Japanese Patent Application mentioned above is to be incorporated into the disclosure by reference.

The invention claimed is:

1. An oxidative chromogenic compound represented by any one of Formulae (A), (B), (C), or (D) shown below having a counter ion selected from the group consisting of alkali metal, alkaline earth metal, and ammonium ions:

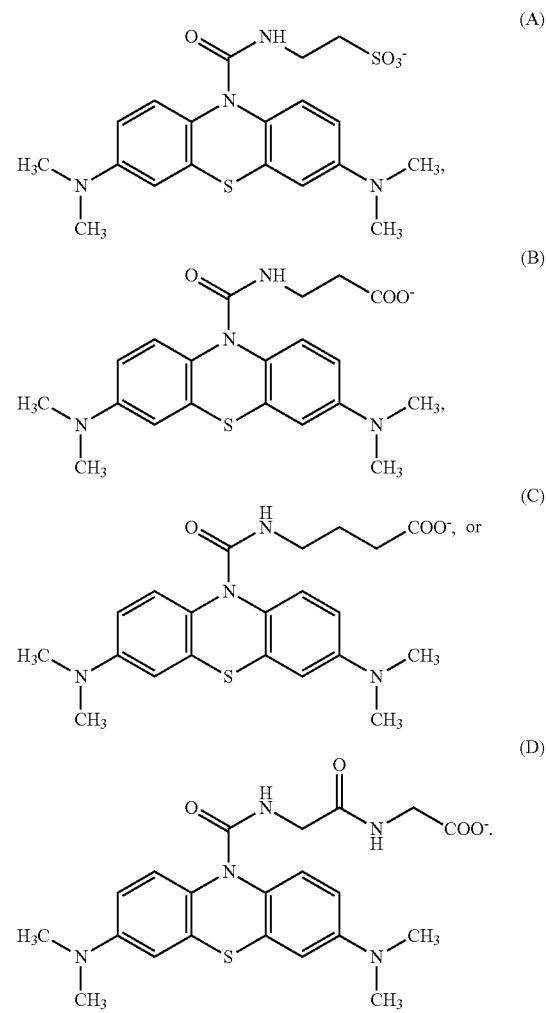

* * * * *